United States Patent [19]

Nilsson

[11] Patent Number: 4,755,175
[45] Date of Patent: Jul. 5, 1988

[54] CATHETER

[76] Inventor: Leif Nilsson, BlÅbärsvägen 1, S-260 40 Viken, Sweden

[21] Appl. No.: 883,173

[22] Filed: Jul. 8, 1986

[30] Foreign Application Priority Data

Jul. 15, 1985 [SE] Sweden .................... 8503480

[51] Int. Cl.⁴ .......................................... A61M 5/005
[52] U.S. Cl. .................... 604/268; 604/102; 604/247; 604/280
[58] Field of Search ............ 604/96, 102, 104, 169, 604/190, 247, 252, 256, 266–268, 280, 264, 126, 129

[56] References Cited

U.S. PATENT DOCUMENTS

| | | | |
|---|---|---|---|
| 1,534,852 | 4/1925 | Hunter | 604/84 |
| 2,610,627 | 9/1952 | Watt et al. | 604/84 |
| 3,314,430 | 4/1967 | Alley et al. | 604/268 |
| 3,583,404 | 6/1971 | McWhorter | 604/266 |
| 3,595,241 | 7/1971 | Sheridan | 604/280 |
| 4,112,924 | 9/1978 | Ferrara et al. | 604/237 |
| 4,227,533 | 10/1980 | Godfrey | 604/266 |
| 4,424,058 | 1/1984 | Parsons et al. | 604/129 |

*Primary Examiner*—Stephen C. Pellegrino
*Assistant Examiner*—Ralph Lewis
*Attorney, Agent, or Firm*—Kane, Dalsimer, Sullivan, Kurucz, Levy, Eisele & Richard

[57] ABSTRACT

A catheter intended for insertion into a canal or canal-like organ, for example into the urethra leading to the urinal bladder of a human being, for the purpose of emptying the contents of the urinal bladder of that person into the catheter. The catheter comprises a preferably flexible, tubular catheter body incorporating a urine inlet and provided with an insertion section together with means for holding the catheter within the urethra. The catheter body also includes a discharge section spaced from the insertion section and intended, for example, for connection to a urine collecting vessel.

According to the invention the interior of the tubular insertion section is arranged to support a sieve or filter element, and means for creating turbulence in the incoming flow to the catheter body, so as to prevent blocking of the inlet opening.

5 Claims, 1 Drawing Sheet

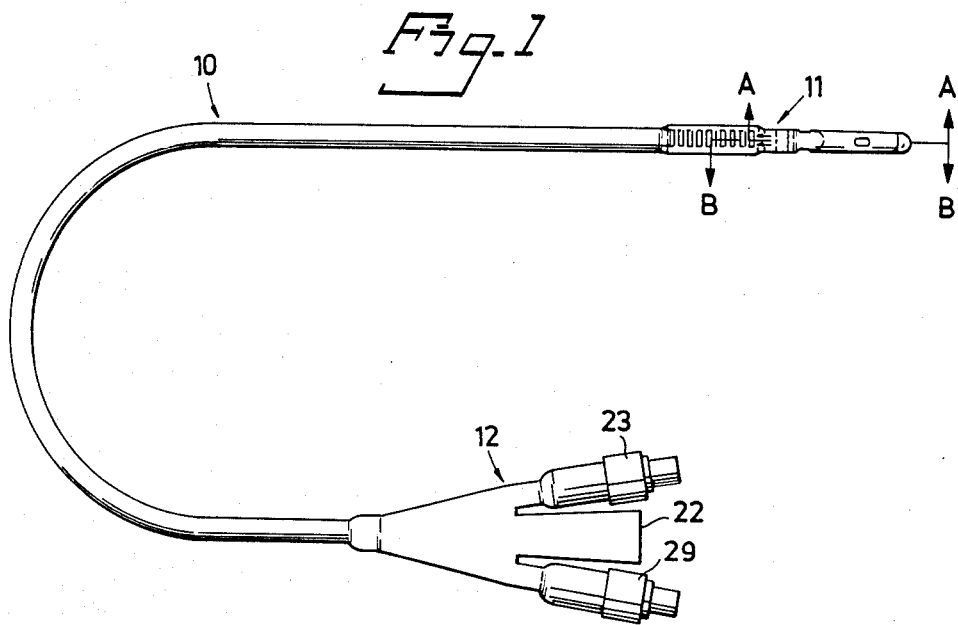
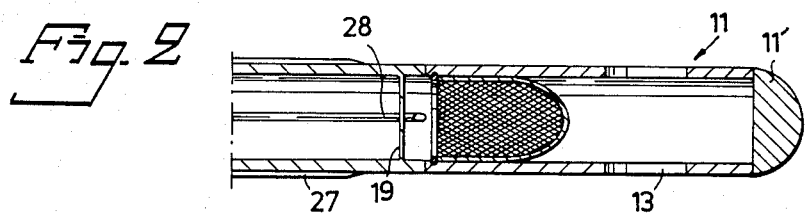
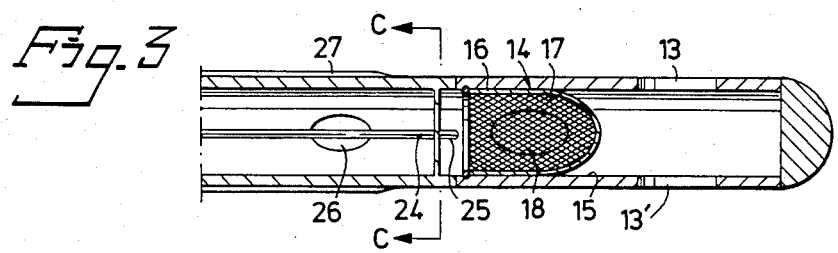
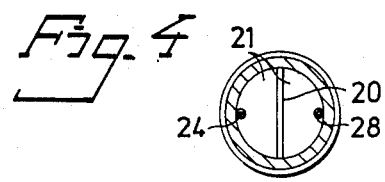

CATHETER

The present invention relates to a catheter intended for insertion into a canal or canal-like organ, for example the urethra of a human being, for the purpose of removing the contents of that person's bladder, the catheter comprising a preferably flexible, tubular catheter body incorporating an insertion section, provided with a urine inlet, means for holding the catheter in the urethra, and a discharge section which is spaced from the inlet section and which is intended for connection, for example, to a urine collecting vessel.

Catheters of this kind are well known in the medical field. These known catheters, however, are encumbered with a number of drawbacks and disadvantages. For example, patients in which such catheters are installed permanently or semi-permanently, by which is meant that the catheters are left inserted for weeks or days in order to constantly drain the bladders of the patients, for example, must be constantly supervised for fear of the catheters becoming blocked with deposits deriving, inter alia, from kidney secretions. Blockaging of the catheter would result in urine remaining in the urinary bladder, which may easily lead to the formation of bacteria, and hence to infection. The walls of the urinary bladder distend, and the bacteria flora is able to settle on damaged mucous membrane and be entrained with the bloodstream, resulting in blood poisoning. The catheter is also liable to become blocked with particles of mucous membrane inadvertently dislodged from the walls of the urethra when inserting the catheter, these particles being liable to block the inlet to the catheter.

A principle object of the invention is therefore to provide means which effectively prevent any form of deposit causing a blockage in the catheter.

A further object is to provide means for creating turbulence in the flow of urine entering the catheter, this turbulence also preventing blockage of the catheter.

Another object is to provide means for facilitating the insertion of a catheter into a canal or canal-like organ and removal of the catheter therefrom, while at the same time greatly reducing the risk of damage to the sensitive mucous membranes.

There is provided in accordance with the invention a catheter intended for insertion into a canal or canal-like organ, for example, into the urethra leading to the urinal bladder of a human being for the purpose of emptying the content of the bladder of said person into the catheter, said catheter comprising a preferably flexible, tubular catheter body incorporating an insertion section provided with a urine inlet and also with means for holding the catheter within the urethra, and further comprising a discharge section which is spaced from the insertion section and which is intended, for example, for connection to a urine collecting vessel. The invention is characterized in that the interior of the tubular insertion section is arranged to support a sieve or filter element and in that means are provided for generating turbulence in the flow of urine to the catheter sufficient to prevent foreign particles in the urine from settling in the urine inlet.

Thus, by incorporating at least two, and preferably three apertures in the insertion section of the catheter in a particular mutual relationship, and arranging a sieve or filter element downstream of the apertures, conditions are created which effectively prevent the apertures in the insertion section from becoming blocked, since the mutual relative arrangement of the apertures is such as to create a certain degree of turbulence in the urine flowing from the urethra into the catheter. Although relatively large particles are liable to enter the catheter through the turbulence created, these particles are held by the filter element and thus remain within the region of the catheter located between the filter element and the inlet of the insertion end of said catheter, while the urine flows through the filter element unimpeded, and into the catheter body.

In accordance with the invention, when the insertion section incorporates three apertures, an effective turbulence is generated by placing two of the apertures opposite to one another and by displacing the third aperture through 90° and also axially in relation to the two first mentioned apertures.

The invention will now be described in more detail with reference to a preferred embodiment of a catheter for removing urine from the urinal bladder of a patient, and also to the accompanying drawings, in which FIG. 1 illustrates a catheter according to the invention;

FIG. 2 is a sectional view taken on the line A—A in FIG. 1;

FIG. 3 is a sectional view taken on the line B—B in FIG. 1; and

FIG. 4 is a sectional view taken on the line C—C in FIG. 3.

The catheter according to the invention comprises a resilient flexible tubular body generally identified by the reference numeral 10. The catheter body may be made of natural rubber, synthetic rubber, an elastomeric substance, or some other suitable synthetic substance, or a mixture of any of said substances.

The catheter body 10 has at one end thereof an insertion section, indicated generally by the reference numeral 11, which in the illustrated embodiment is intended for insertion into the urethra (not shown) of a patient. The opposite end of the catheter is provided with a discharge section 12. The catheter is normally made in one single piece. The insertion section 11, shown in detail in FIGS. 2 and 3, has a closed end-part 11'.

Arranged in the insertion section 11 in the vicinity of the closed end-part 11' are apertures 13,13', which are located opposite to one another. These apertures 13,13' are intended to accommodate urine which flows from the urinary bladder into the urethra. Arranged within the insertion section 11 downstream of the apertures 13,13' is a sieve or filter element 14, which comprises a circular frame 16, which is held firmly clamped against the inner wall 15 of the insertion section, and a fine mesh filter 17 which is directed towards the apertures 13,13'. The filter element 14, thus has a zig-zag construction and, in the illustrated embodiment, located within the region of the filter element in the insertion section 11 is a further aperture 18, which communicates with the urethra (not shown) when the catheter is inserted in position. The described arrangement allows urine to flow from the urethra into the catheter through the three apertures 13,13' and 18, the mutual relative positions of which are such as to create a certain amount of turbulence in the urine flow, therewith counteracting blockage of the apertures by deposits deriving from kidney secretions or from damaged urethra mucous membrane. These deposits accompany the urine into the catheter instead, and are duly filtered out by the filter element 14, therewith preventing the deposits from travelling further through the catheter. Consequently, deposits of a larger particle size will remain in the upstream end of the insertion section 11. It has been found that an effective turbulence is created when three apertures are utilized and when two of these apertures are located opposite one another and the third is displaced axially and rotated through 90° relative to the two apertures first mentioned. Notwithstanding this, it is conceivable to use solely one aperture which is designed to co-act with turbulence generating means, such as a baffle plate, in the immediate vicinity thereof, the important thing being that a satisfactory turbulence is generated. The primary object of the invention is therewith fulfilled.

A further drawback to known catheters, and one which might also be found with the novel catheter construction aforedescribed, is that a continuous flow of urine from the bladder, through the urethra and out into the catheter, and from there to a collecting vessel, requires the bladder to work continuously. Consequently, a person who permanently requires a catheter is liable to contract so-called atrophy of the bladder if the catheter is used for long periods of time, this degenerative disease very often being difficult to treat successfully.

In order to overcome this drawback, the insertion section 11 of the catheter body 10 has arranged therein an openable and closeable valve means 19, which is located downstream of the communication apertures 13,13' and 18, and also preferably downstream of the filter element 14. The valve means 19 is intended to operate automatically, and to this end is constructed in a manner which enables it to be switched from a closed position, in which it normally blocks the passage of the urine through the catheter body, to an open position by the pressure exerted on the valve wall by a predetermined volume of urine flowing on the urethra through the apertures 13,18 and collecting in the forward part of the insertion section. When the pressure on the valve wall has reached the aforesaid predetermined value, the valve body is rotated about its axis and the enclosed urine flows out through the catheter. When the pressure is relieved the valve closes and the described procedure is repeated.

Such a valve arrangement functions in a manner similar to the natural urine drainage process of a healthy person. It would seem that the problem relating to so-called atrophy of the bladder is therewith eliminated.

Such self-closing and self-opening valves are known to the art and can be likened to a swing door, or to a saloon-bar door, the two leaves of which swing away in response to pressure and swing back when the pressure is relieved.

Although the construction of the valve as such does not form part of the invention, which resides in part simply in the inclusion of such a valve as a solution to the aforementioned problems, an embodiment of one such valve means 19 is illustrated in FIG. 4. In the illustrated valve embodiment, the valve means 19 comprises a so-called swinging axle 20 having mounted thereon two wings 21, the extremities of which sealingly engage the inner wall surfaces of the catheter body 10, the wings 21 being mounted on the swinging axle 20 in a manner to obtain the aforesaid self-opening and self-closing effect. Although not shown, the two wings 21 of the valve means 19 may each be mounted on a respective swinging axle provided on mutually opposite sides of the inner wall surface of the catheter body. Conceivably these latter swinging axles may be formed by the actual material of the catheter body, as can also the wings joined to said axles. The valve means 19 thus obtains a self-closing function, i.e., the valve body constantly strives to take its closed position, but can be moved to its open position by the pressure exerted on the walls of the valve means by the urine collected in the insertion section of the catheter.

The exemplifying embodiment of the catheter illustrated in the drawing is referred to as a so-called three-way catheter, by virtue of the configuration of the discharge section 12 (FIG. 1). Thus, the catheter body 10 branches at the discharge section 12 into a central outlet 22 and two side branch pipes 23 and 29. The central outlet 22 is intended to conduct the urine exiting from the catheter body 10, and is connected to a suitable urine collecting vessel. The branch pipe 23 is connected to a very fine tube 24 which extends through the interior of the catheter body 10 in abutment with an inner wall thereof. The closed end 25 of the hose 24 is located upstream, or alternatively downstream of the valve means 19. The hose 24 is intended to be filled with liquid, e.g., water, which is introduced through an inlet 23 and which is intended to pass out through an outlet 26 so as to distend sac-like wall portions 27 and therewith form protrusions which abut the mucous membrane of the urethra, therewith locating the catheter in position in the urethra for removal of urine from the bladder of a patient. The inclusion of such sac-like portions which, when inflated, form means for clamping the catheter in position are known to the art.

The branch pipe 29 connects in the catheter body 10 with a fine hose 28, similar to the hose 24, which discharges downstream of the filter element 14. When the catheter is to be inserted into the urethra of a patient, liquid, e.g., water, is introduced under pressure into the branch pipe 27. This liquid flows out through the exit orifice of the hose 28 and endeavours to depart through the apertures 13,13',18 and enter the urethra of the patient whose bladder is to be drained. The liquid acts as a lubricant against the mucous membrane of the urethra and the insertion section of the catheter body and will therefore protect to a large extent the sensitive mucous membrane of the urethra. This latter arrangement can also be used advantageously for rinsing the filter element 14 and that part of the insertion section 11 located upstream of the filter element 14.

Although it is assumed here that the sieve or filter element 14 can be removed from its working location in the insertion section, it will be appreciated that the filter element may also be permanently attached to the insertion section. The aforesaid arrangement can also be used to rinse a urinal bladder upon which surgery has been performed. The exit orifice of the branch pipe 29 may also be connected to a source of vacuum so as to create an area of sub-pressure in the catheter and therewith remove larger particles from the urinal bladder and urethra by suction. When using the catheter for this purpose the filter element 14 is preferably removed.

When it is desired to X-ray the hypogastrium, or abdominal region, of a patient while leaving a catheter inserted, the catheter material may be colored in a suitable manner to permit X-ray plates to be readily discerned and to show the presence of a catheter in the urethra.

The described and illustrated catheter can be modified within the scope of the following claims. The position of the filter element 14 is mainly determined by the positions of the apertures 13,13',18, and also to a certain extent by the position of the abutment protrusions 27.

I claim:

1. A catheter for insertion into a urethra to facilitate drainage of urine from a urinary bladder, comprising:

a flexible tubular catheter body defining a lumen and having proximal and distal ends, the distal end comprising a urine inlet section and means for fixedly positioning the catheter within the urethra and the proximal end comprising a control section having discharge means connectable to a urine collection vessel, wherein filter means are positioned within the urine inlet section across the fluid path of urine through the lumen, wherein the inlet urine section has a closed distal end and three urine inlet apertures, two of which are positioned opposite one another and the third of which is positioned at 90° relative to the first and second urine inlet apertures to cause sufficient turbulence in the flow of urine within the catheter to prevent undesired particles from settling within the urine inlet section to block urine flow, and wherein valve means are positioned within the lumen downsteam and proximal of the filter means, said valve means having valve walls which are in sealing abutment with the inner surface of the catheter body and which are reclosably openable to permit flow of the urine when pressure exerted on the valve walls by the urine reaches a predetermined value.

2. The catheter assembly of claim 1, wherein the means for fixedly positioning the catheter within the urethra comprises an inflatable balloon means in fluid connection with a hose within said catheter which is in fluid connection with an inflatation/deflation port on the control means.

3. The catheter assembly of claim 1, wherein the lumen comprises a flushing hose having distal and proximal ends, the distal end of said hose ending inbetween the valve means and the filter means and the proximal end of said hose being in fluid communication with a port in the control section.

4. The catheter assembly of claim 1, wherein the filter means is detachable.

5. A catheter for insertion into a urethra to facilitate drainage of urine from a urinary bladder, comprising:

a flexible tubular catheter body defining a lumen and having proximal and distal ends, the distal end comprising a urine inlet section and means for fixedly positioning the catheter within the urethra and the proximal end comprising a control section having discharge means connectable to a urine collection vessel, wherein filter means are positioned within the urine inlet section across the fluid path of urine through the lumen; wherein the inlet urine section has a closed distal end and three urine inlet apertures, two of which are positioned opposite one another and the third of which is positioned at 90° relative to the first and second urine inlet apertures to cause sufficient turbulence in the flow of urine within the catheter to prevent undesired particles from settling within the urine inlet section to block urine flow; wherein valve means are positioned within the lumen proximal to the filter means, said valve means having valve walls which are in sealing abutment with the inner surface of the catheter body and which are reclosably openable to permit flow of the urine when pressure exerted on the valve walls by the urine reaches a predetermined value; wherein the means for fixedly positioning the catheter within the urethra comprises an inflatable balloon means in fluid connection with a first hose within said catheter which is in fluid connection with an inflation/deflation port on the control means; and wherein the lumen comprises a second hose having distal and proximal ends, the distal end of said second hose ending distal ot the valve means and proximal to the filter means and the proximal end of said second hose being in fluid communication with a port in the control section.

* * * * *

UNITED STATES PATENT AND TRADEMARK OFFICE
CERTIFICATE OF CORRECTION

PATENT NO. : 4,755,175
DATED : July 5, 1988
INVENTOR(S) : Leif Nilsson

It is certified that error appears in the above-identified patent and that said Letters Patent is hereby corrected as shown below:

Col. 5, Claim 1, line 16, "closed" should read --a closed--.

Col. 6, Claim 5, line 38, "ot" should read --to--.

Signed and Sealed this

First Day of November, 1988

*Attest:*

DONALD J. QUIGG

*Attesting Officer*  *Commissioner of Patents and Trademarks*